(12) United States Patent
Sohngen

(10) Patent No.: US 6,921,400 B2
(45) Date of Patent: *Jul. 26, 2005

(54) MODULAR INTRAMEDULLARY NAIL

(76) Inventor: Gary W. Sohngen, 3722 Weymouth Ave., San Pedro, CA (US) 90731

( * ) Notice: Subject to any disclaimer, the term of this patent is extended or adjusted under 35 U.S.C. 154(b) by 0 days.

This patent is subject to a terminal disclaimer.

(21) Appl. No.: 10/449,337

(22) Filed: May 30, 2003

(65) Prior Publication Data

US 2003/0195515 A1 Oct. 16, 2003

Related U.S. Application Data

(63) Continuation of application No. 09/694,666, filed on Oct. 23, 2000, now abandoned.
(60) Provisional application No. 60/160,656, filed on Oct. 21, 1999.

(51) Int. Cl.⁷ .................................... A61B 17/72
(52) U.S. Cl. .................. 606/64; 606/62; 606/67
(58) Field of Search ..................... 606/62, 64, 67, 606/68

(56) References Cited

U.S. PATENT DOCUMENTS

| | | |
|---|---|---|
| 2,518,019 A | 8/1950 | Kane |
| 3,433,220 A | 3/1969 | Zickel |
| 4,622,959 A | 11/1986 | Marcus |
| 4,776,330 A | 10/1988 | Chapman et al. |
| 4,805,607 A | 2/1989 | Engelhardt et al. |
| 4,827,917 A | 5/1989 | Brumfield |
| 4,875,475 A | 10/1989 | Comte et al. |
| 4,877,019 A | 10/1989 | Vives |
| 4,946,459 A | 8/1990 | Bradshaw et al. |
| 4,978,349 A | 12/1990 | Frigg |
| 5,032,125 A | 7/1991 | Durham et al. |
| 5,034,013 A | 7/1991 | Kyle et al. |
| 5,074,882 A | 12/1991 | Grammont et al. |
| 5,122,141 A | 6/1992 | Simpson et al. |
| 5,127,913 A | 7/1992 | Thomas, Jr. |
| 5,201,735 A | 4/1993 | Chapman et al. |
| 5,454,813 A | 10/1995 | Lawes |
| 5,458,600 A | 10/1995 | Stapert et al. |
| 5,489,284 A | 2/1996 | James et al. |
| 5,505,733 A | 4/1996 | Justin et al. |
| 5,505,734 A | 4/1996 | Caniggia et al. |
| 5,549,610 A | 8/1996 | Russell et al. |
| 5,569,249 A | 10/1996 | James et al. |
| 5,620,445 A | 4/1997 | Brosnahan et al. |
| 5,653,709 A | 8/1997 | Frigg |
| 5,658,287 A | 8/1997 | Hofmann et al. |
| 5,704,939 A | 1/1998 | Justin |
| 5,766,174 A | 6/1998 | Perry |
| 5,855,579 A | 1/1999 | James et al. |
| 5,928,235 A | 7/1999 | Friedl |
| 5,935,127 A | 8/1999 | Border |
| 6,004,324 A | 12/1999 | Gahr et al. |
| 6,106,528 A * | 8/2000 | Durham et al. ............... 606/64 |
| 6,228,086 B1 | 5/2001 | Wahl et al. |
| 6,261,290 B1 | 7/2001 | Friedl |

FOREIGN PATENT DOCUMENTS

| | | |
|---|---|---|
| JP | 9066061 | 3/1997 |
| WO | WO 94/13219 | 6/1994 |
| WO | WO 96/35387 | 11/1996 |

* cited by examiner

Primary Examiner—Cary E. O'Connor
Assistant Examiner—Candice C. Stokes
(74) Attorney, Agent, or Firm—Burgess Law Office, PLLC

(57) ABSTRACT

An intramedullary nail for repair of bone fractures. The intramedullary nail is of a modular configuration including a nail member having a chamber formed on the proximal end thereof. An insert having at least one opening therein for receiving a bone screw or fastener is disposed within the chamber and is secured therein by a locking ring. Accordingly, various inserts may be used to achieve selected bone screw or fastener configurations.

15 Claims, 13 Drawing Sheets

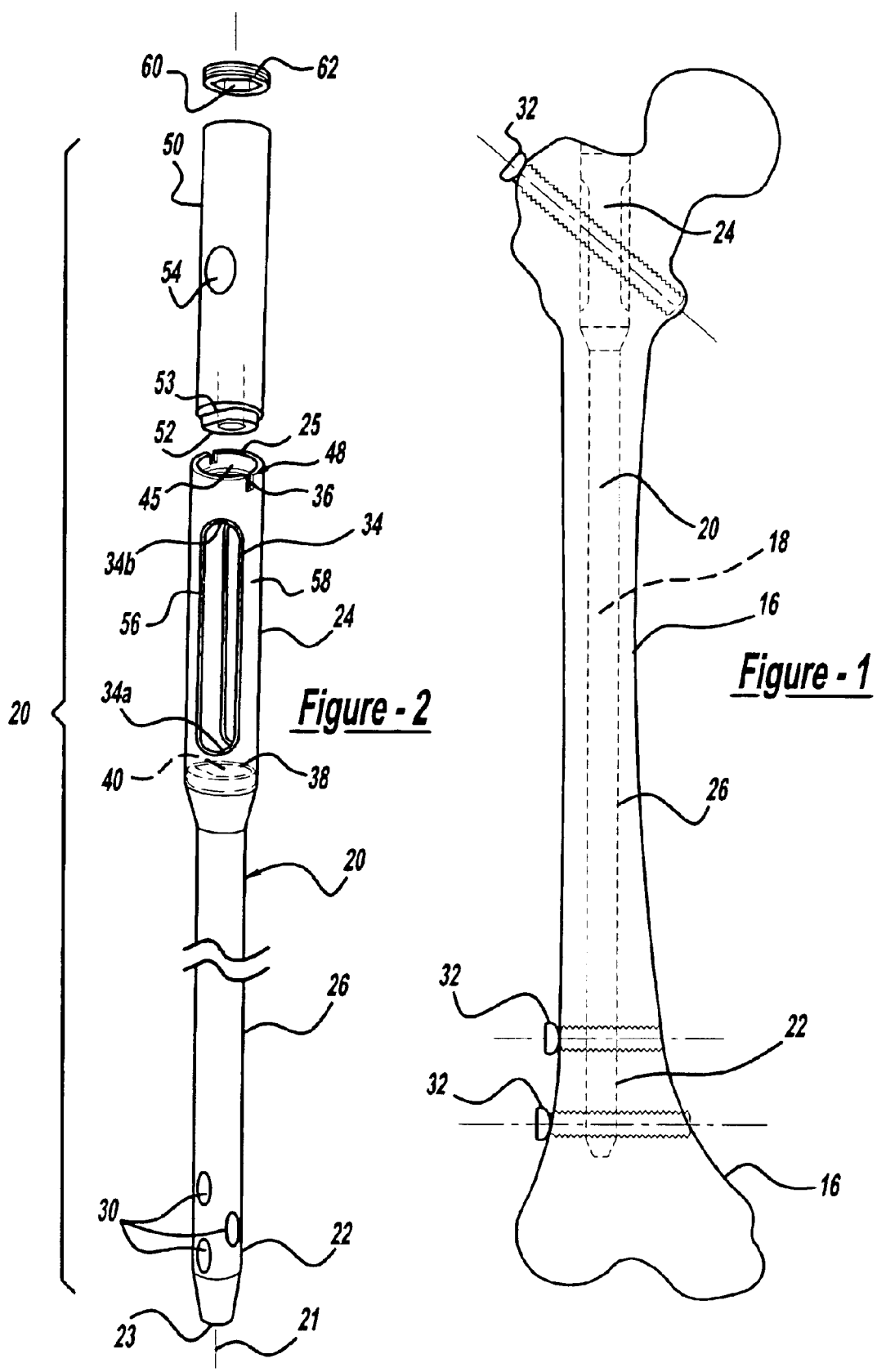

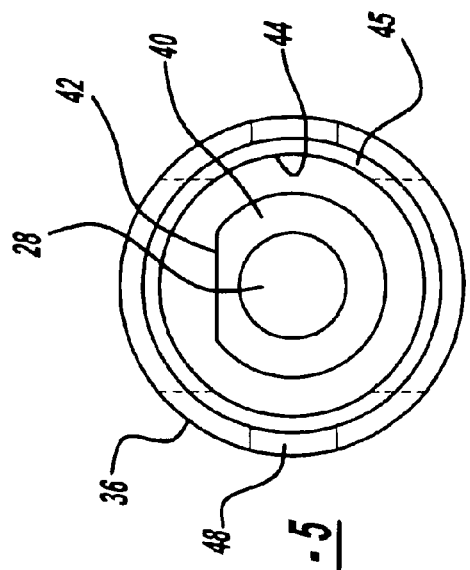
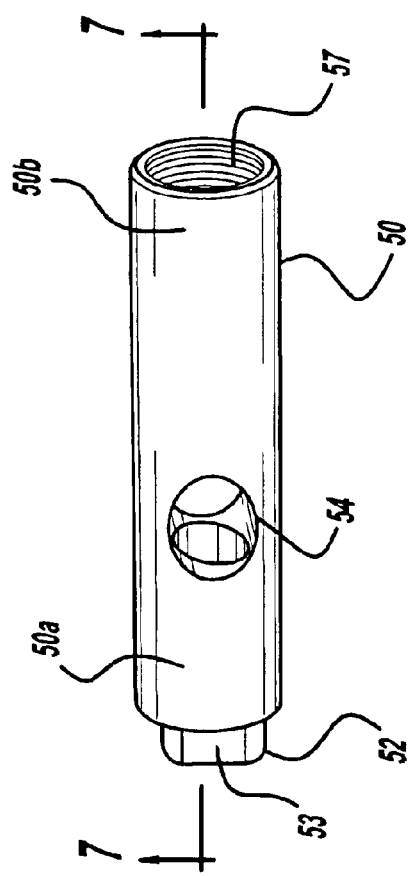
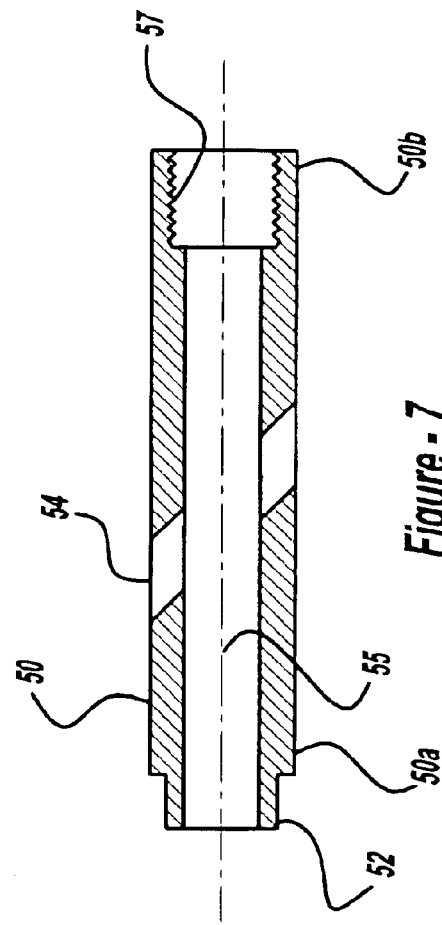

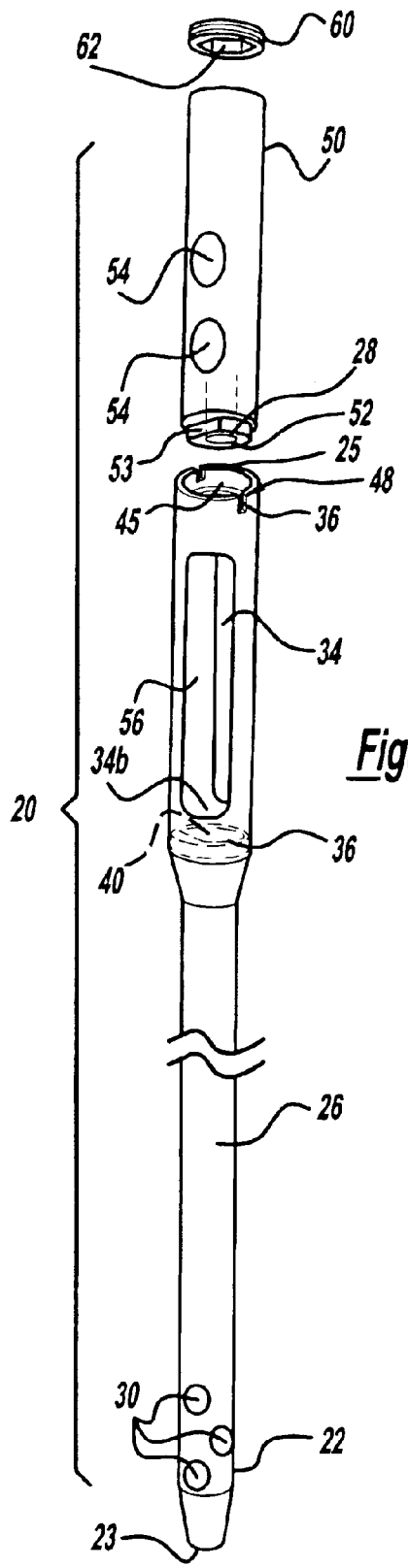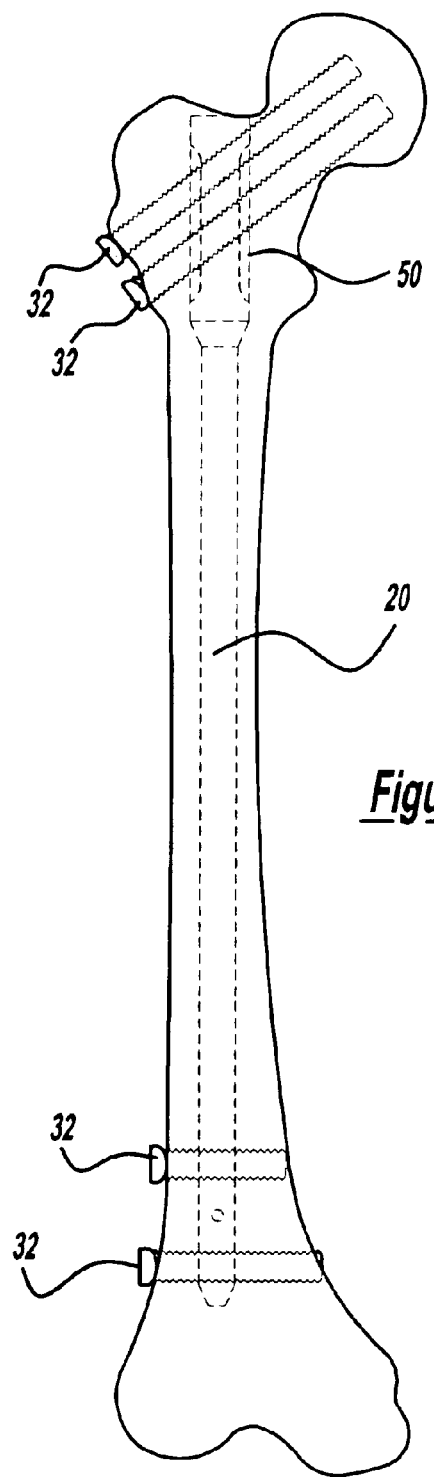
Figure - 8
Figure - 9

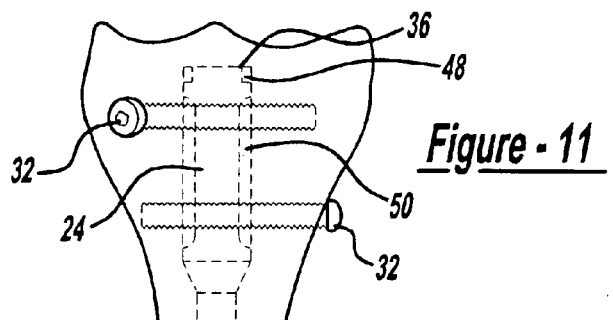
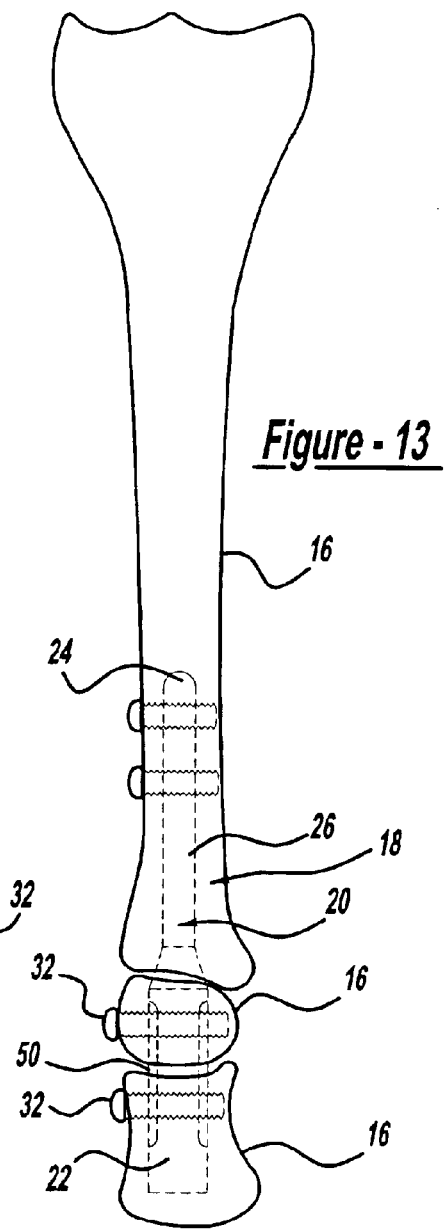
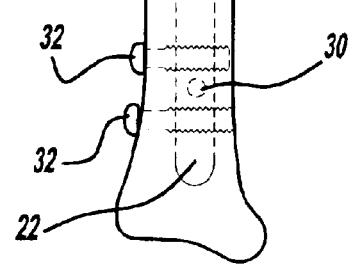
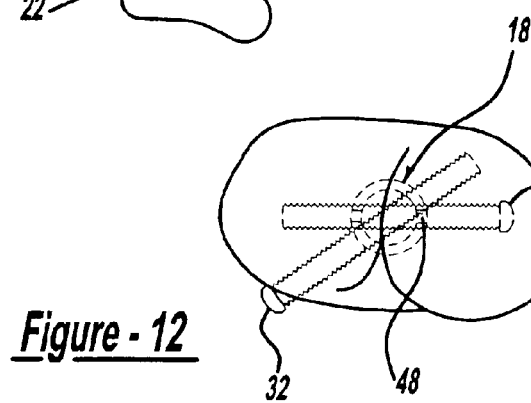

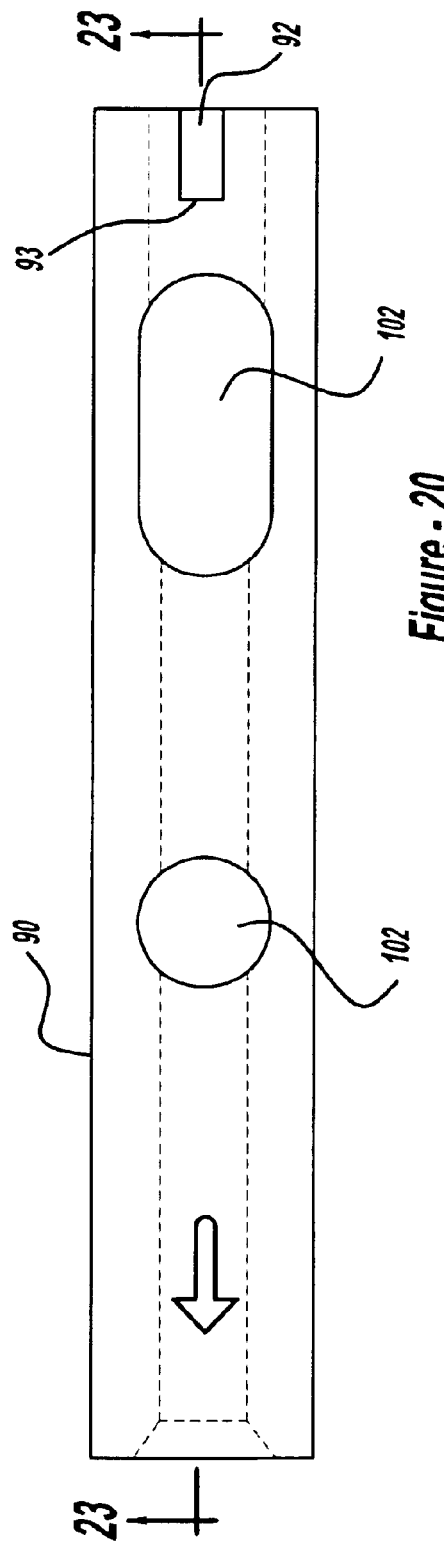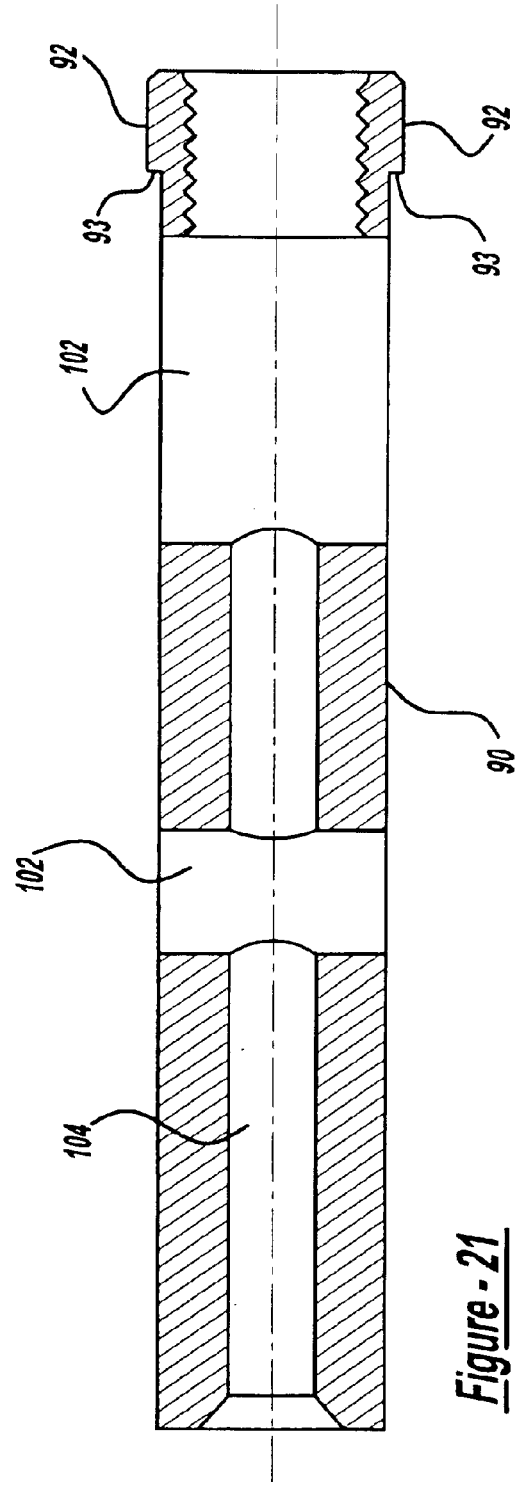

MODULAR INTRAMEDULLARY NAIL

This is a continuation-in-part of Ser. No. 09/694,666 filed Oct. 23, 2000, now abandoned, which claims benefit of 60/160,656 filed Oct. 21, 1999.

BACKGROUND OF THE INVENTION

1. Field of the Invention

The present invention relates generally to an intramedullary nail for the repair of bone fractures, and more specifically, to a modular nail that allows a surgeon to use different inserts to achieve a selected nail configuration for use with a particular type of fracture.

2. Description of the Related Art

Intramedullary nails are proven devices that provide a temporary fixation means to stabilize a fracture until the fracture heals. The nail is inserted in the marrow canal of the bone and is positioned to span the fracture. The nail is received and anchored within the bone via bone screws placed through aligned apertures in the nail.

The screws are usually inserted in the proximal and distal ends of the nail and in the case of the proximal end, the orientation of the screws depends upon the particular configuration needed including antegrade, reconstruction and retrograde. Thus, different nails are required for different configurations, i.e., fractures. Many hospitals stock complete nail systems that are designed to handle only specific fractures. Not only does each nail system require different components, many also require unique instrumentation systems intended for use with only one type of nail. This results in increased and unnecessary inventory that correspondingly increases the cost to the hospital and patient.

Accordingly, it is advantageous to have an intramedullary nail with greater modularity that provides a surgeon more options enabling them to handle a wider range of fractures while streamlining the components necessary to do so.

SUMMARY OF THE INVENTION

The present invention is directed to a modular intramedullary nail for use in stabilizing a fracture until healing has occurred. The modular intramedullary nail of the present invention includes an elongated nail member having a distal end and a proximal end. The proximal end includes a chamber located thereon. The chamber is configured to receive an insert having an opening therein. The opening is configured to receive a screw used to secure the nail member to the bone to stabilize the fracture. A locking ring engages the chamber to secure the insert within the chamber.

In accordance with the present invention, depending upon a patient's requirements, by using the various inserts, selected screw configurations can be achieved and chosen preoperatively and then assembled before insertion. Use of multiple inserts with a single nail member allows a surgeon to place screws at various angles and in various locking configurations including antegrade, reconstruction and retrograde along with dynamic oblique locking and dynamic transverse locking.

The present invention will be readily appreciated as the same becomes better understood after reading the subsequent description taken in conjunction with the accompanying drawings.

BRIEF DESCRIPTION OF THE DRAWINGS

FIG. 1 is a diagrammatic front view of a modular nail according present invention shown implanted within a femur in antegrade configuration;

FIG. 2 is an exploded perspective view of the modular nail illustrated in FIG. 1;

FIG. 5 is a top view of the nail FIG. 3 of the modular nail illustrated in FIG. 1;

FIG. 6 is a perspective view of an insert for use with the nail member of the modular nail illustrated in FIG. 1;

FIG. 7 is a sectional view of the insert of FIG. 6 taken along line 7—7 of FIG. 5;

FIG. 8 is an exploded perspective view of a second embodiment of the modular nail according to the present invention;

FIG. 9 is a diagrammatic front view of the second embodiment of the present invention according to FIG. 8 shown implanted within a femur in a reconstructive configuration;

FIG. 11 is a diagrammatic rear view of a fifth embodiment of the present invention shown implanted within a tibia;

FIG. 12 is a diagrammatic top view of the fifth embodiment of the present invention shown implanted within a tibia;

FIG. 13 is a diagrammatic rear view of a sixth embodiment of the present invention shown implanted within an ankle joint;

FIG. 20 is a side view of an insert for use with the nail member of the modular nail illustrated in FIG. 15;

FIG. 21 is a cross-sectional view of the insert of FIG. 20 taken along line 21—21 of FIG. 20;

DETAILED DESCRIPTION OF THE PREFERRED EMBODIMENT(S)

Figure 3:
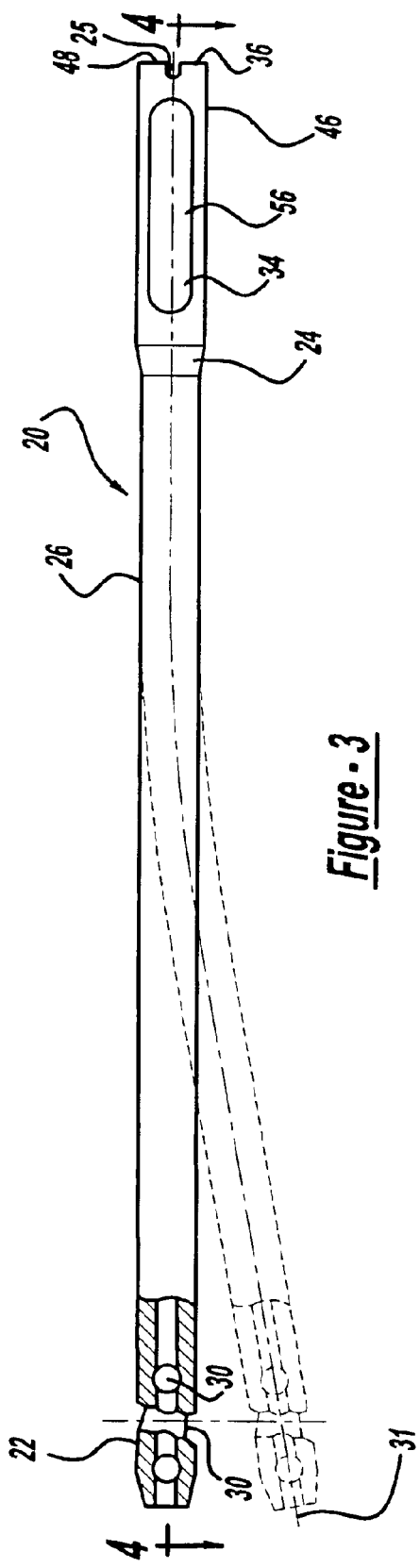
FIG. 3 is a side view of a nail member of the modular nail illustrated in FIG. 1 with a portion shown in section to illustrate a feature thereof and further including a portion shown in phantom to illustrate a further feature thereof.
Figure 4:
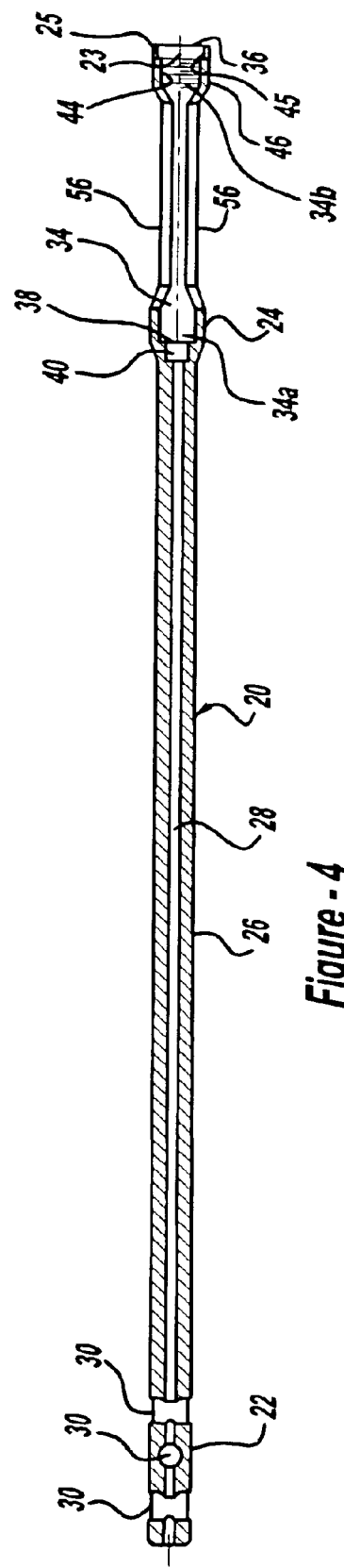
FIG. 4 is a sectional view of the nail member of FIG. 3 taken along line 4—4 of FIG. 3.

FIGS. 1–4 show a modular intramedullary nail 18 according to one embodiment of the present invention placed an assembled condition within a bone 16. The modular intramedullary nail 18 includes a nail member 20 formed of a metallic alloy such as a titanium alloy. The nail member 20 includes a distal end 22, a proximal end 24 and a middle portion 26. The distal end 22 includes a leading edge 23 and the proximal end 24 includes a trailing or rear edge 25. A passageway 28 extends longitudinally through the nail member 20 between the proximal end 24 and the distal end 22. The passageway 28 receives insertion and extraction instrumentation, such as a guidewire (not shown), used to position the nail member 20 within the bone 16. Typically the leading edge 23 of the nail member 20 follows the path of the guide wire and is inserted into the bone 16 first.

As illustrated in FIG. 1, a plurality of fasteners 32, illustrated herein as bone screws, extend through the nail member 20 and into the bone 16 to secure the nail member 20 in place. Other fasteners such as blades, beams, pins or wires could also be used.

As shown in FIG. 2, the distal end 22 of the nail member 20 includes a plurality of holes 30. The holes 30 typically extend transverse the longitudinal axis 21 of the nail member 20. The fasteners 32 extend through the holes 30 to secure the lower or distal end 22 of the nail member 20 to the bone 16. Following the preferred procedure, the holes 30 are positioned transverse to the longitudinal axis of the bone 16. As shown in FIG. 3, the nail member 20 may be bowed a slight amount as shown by the plane 31 to account for the natural curvature of the bone 16. If so, one of the holes 30 is drilled at a slight angle to the longitudinal axis 21 of the nail member 20 such that the holes 30 and corresponding fasteners 32 remain perpendicular to the longitudinal axis of the bone 16 even though the distal end 22 of the nail member 20 is bowed.

Turning to the opposite or proximal end 24, the proximal end 24 includes a barrel or chamber 34 located thereon. The chamber 34 includes a distal end 34a and a proximal end 34b. An opening 36 located in the proximal end 34b of the chamber 34 provides access to the chamber 34. As shown, the opening 36 is located at the rear edge 25 of the nail member 20. In addition, the chamber 34 includes a socket 40 for a purpose to be set forth later. The chamber 34 also has an inner surface 44. The inner surface 44 of the proximal end 34b of the chamber 34 contains a plurality of threads 45. Notches 48 are found in the trailing or rear edge 25 of the proximal end 24. The insertion and extraction instruments (not shown) are configured to pass through the longitudinal passageway 28 and engage the notches 48 to rotate and properly position the nail member 20 within the bone 16.

An insert 50, shown in FIGS. 6–7, having a distal end 50a and a proximal end 50b, is placed within the chamber 34. The insert 50 has a locking projection 52 located on the distal end 50a thereof. The locking projection 52 as shown in FIG. 6 has a cylindrical shape with a flat side 53. The shape of the locking projection 52 corresponds with the shape of the socket 40 in the chamber 34. It should be appreciated that one purpose of the locking projection 52 and corresponding socket 40 is to properly orient the insert 50 within the chamber 34. In some instances, another purpose is to support the distal end 50a of the insert 50. Accordingly, various other shapes and configurations may also be used. For example, the locking projection 52 and corresponding socket 40 may have square, hexagonal, star, triangular or other configurations.

The insert 50 further includes an opening 54 extending therethrough. The opening 54 is oriented such that when the insert 50 is placed within the chamber 34, the opening 54 aligns with a longitudinal slot 56 extending through the wall 58 of the nail member 20 against the chamber 34. Additional fasteners 32 pass through both the opening 54 in the insert 50 and the slots 56 to anchor the proximal end 24 of the nail member 20 to the bone 16. The insert 50 may contain multiple openings 54 oriented in any number of angular configurations with respect to the longitudinal axis 21 of the nail member 20. The insert 50 further includes a longitudinal passageway 55 extending through the insert 50. The longitudinal passageway 55 is coincident with the passageway 28 in the nail member 20 thereby enabling passage of the guide wire or other insertion or extraction instruments through the insert 50. The insert 50 further includes a threaded bore 57 located in one end thereof. The threaded bore 57 may receive a correspondingly threaded tool (not shown) to attach insertion or extraction instrumentation of the assembled modular implant. Accordingly, various inserts 50 can be used to achieve a modular intramedullary nail 18 that may be used with various bones and fracture types. As set forth previously, the fasteners 32 used herein are disclosed as bone screws. However, other fasteners 32 such as blades, beams, pins, or wires could also be used.

A locking member 60 having a plurality of threads 62 on its outer diameter engages the threads 45 located in the proximal end 34b of the chamber 34. When tightened, the locking member 60 secures the insert 50 within the chamber 34. While the locking member 60 is disclosed herein as a threaded ring, other locking members such as snap rings, pins, plugs or any other device that secures the insert 50 in place could also be used. As shown in the present embodiment, an aperture or longitudinal passageway 61 located in the center of the locking member 60 provides a path through which the guide wire or other instrumentation passes during insertion or extraction of the modular intramedullary nail 18. The aperture 61 may be formed in the shape of a socket 62, which in the instant embodiment, is hexagonally shaped. Accordingly, a suitable tool is inserted into the drive socket 62 to tighten the locking member 60 and secure the insert 50 in position within the chamber 34.

The present invention allows a surgeon to address a wide variety of fractures with a single modular intramedullary nail for the femur and a single modular intramedullary nail for the tibia. As shown in FIGS. 8–13, the insert 50 and corresponding nail member 20 are selected based upon the various configurations needed for the femur, including antegrade, reconstruction and retrograde. Accordingly, the possibilities for the orientation of the fasteners 32 placed on the proximal end 24 of the nail member 20 are endless depending upon the particular insert 50 chosen for use with the nail member 20. Such a modular system allows a surgeon more options to handle a wider range of installations or techniques using one system with reduced implant inventory and instrumentation.

As disclosed, the modular intramedullary nail 18 according to one embodiment of the present invention includes a primary nail member 20 wherein the proximal end 24 of the nail member 20 has a chamber 34 that enables use of an insert 50 with different opening 54 configurations. The inserts 50 are keyed with a locking projection 52 received in a corresponding or complementary shaped socket 40 in the chamber 34 to orient the insert 50. A locking member 60 engages the nail member 20 to secure the insert 50 in the chamber 34.

In accordance with a further aspect of the invention, the insert 50 may be made of a resorbable material for dynamization. That is, the loads carried by the fasteners 32 and nail member 20 are slowly decreased as the resorbable material is absorbed into the body. Accordingly, as the fracture heals the load is gradually transferred to the fracture.

Additionally, the insert 50 may be made of any implantable polymer so that the surgeon may drill through the insert 50 to position and locate the fasteners. This provides the surgeon with greater flexibility as each insert may be customized for the particular needs of the patient.

Figure 10:
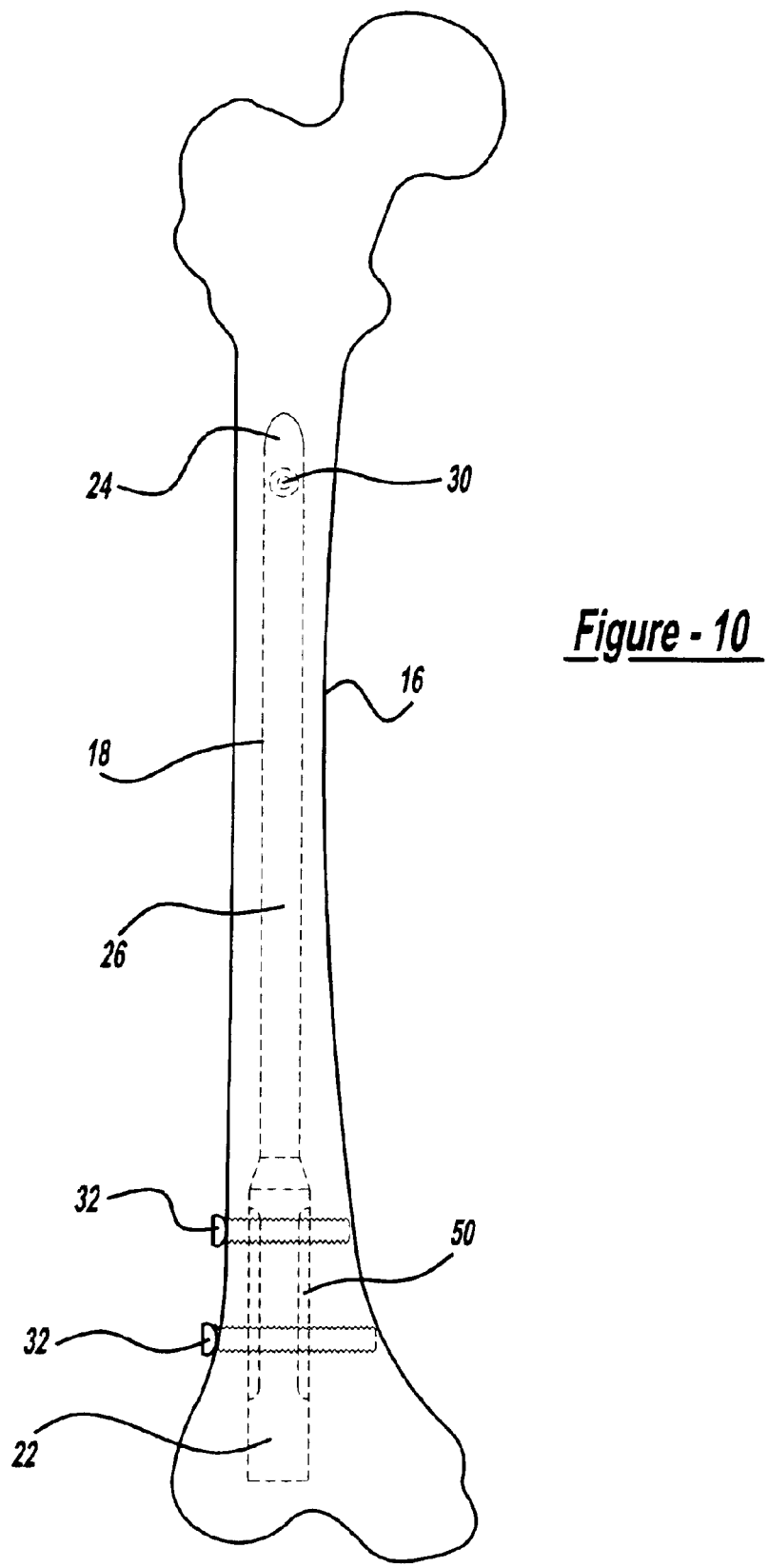
FIG. 10 is a diagrammatic front view of a fourth embodiment of the present invention shown implanted within a femur in a retrograde configuration.

Accordingly, pursuant to one embodiment of the invention, the modular intramedullary nail 18 includes a nail member 20 and an insert 50 received within the chamber 34 in the proximal end 24 of the nail member 20. While one embodiment of the modular intramedullary nail 18 a shown with the insert 50 placed in the proximal end 24 of the nail member 20, this is for the purpose of illustration only. It is not necessary that the insert 50 always be placed in the proximal end 24, see for example FIG. 10 illustrating a retrograde technique. Finally, the drawings shown herein are for illustrative purposes. A surgeon can vary the number of fasteners used, along with the location or orientation of the fasteners. In short, the modular intramedullary nail 18 of the present invention is a device that allows a surgeon to select and place a different insert 50 within the chamber 34 of the nail member 20 to achieve a particular nail configuration suitable for a particular fracture.

Figure 14:
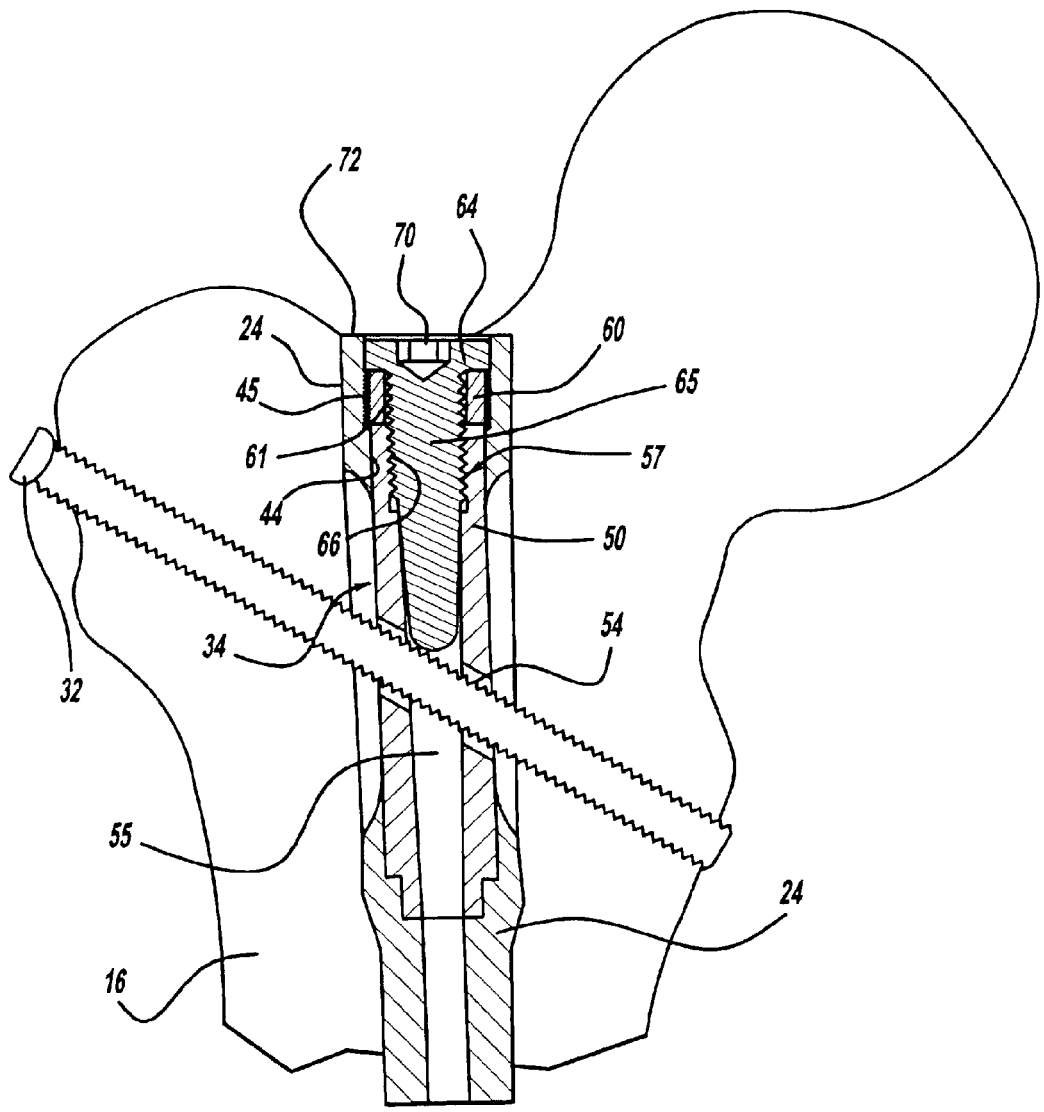
FIG. 14 is a partial sectional view of a seventh embodiment of the present invention shown implanted within a femur.

FIG. 14 shows a further embodiment of the present invention including an end cap 64. An elongated post portion 65 of the end cap 64 extends inwardly into the chamber 34. A plurality of threads 66 are formed on the post portion 65. The threads 66 engage the complementary threaded bore 57 of the insert 50. As illustrated in FIG. 14, the non-threaded part of the post portion 65 of the end cap 64 fits through the longitudinal passageway 55 of the insert 50 and engages the fastener 32 located in the opening 54 of the insert 50. The post portion 65 of the end cap 64 engages the fastener 32 to lock the fastener 32 in position and prevent the fasteners 32 from rotating or working loose. As with the foregoing embodiments, a locking member 60 secures the insert 50 within the chamber 34. The post portion 65 of the end cap 64 extends through the aperture 61. The end cap 64 may be flush or extend radially outward beyond the diameter of the proximal end 24 of the nail member 20. The end cap 64 prevents bone growth into the nail member 20.

Accordingly, prior to installation in the bone 16, the modular intramedullary nail 18 is assembled by securing an insert 50 within the chamber 34 of the nail member 20 with a locking member 60. After assembly, the intramedullary nail 18 is inserted into the bone 16 and corresponding bone screws or fasteners 32 extend through the opening 54 in the insert 50 to fasten the intramedullary nail 18 to the bone 16. Once the fasteners 32 are in place, the end cap 64 is then threadably received in the insert 50 and tightened, using a suitable tool engaging a drive socket 70 formed in the upper surface 72 of the end cap 64, until the post portion 65 engages the bone screw or fastener 32.

It should be understood that the threads 66 of the post portion 65 may be of a size and diameter wherein they engage the threads 57 of the insert 50 rather than the threads 45 of the chamber 34. Thus, the non-threaded part of the post portion 65 may extend through the aperture 61 in the locking member 60 and into the longitudinal passageway 55 of the insert 50.

Figures 15, 23:
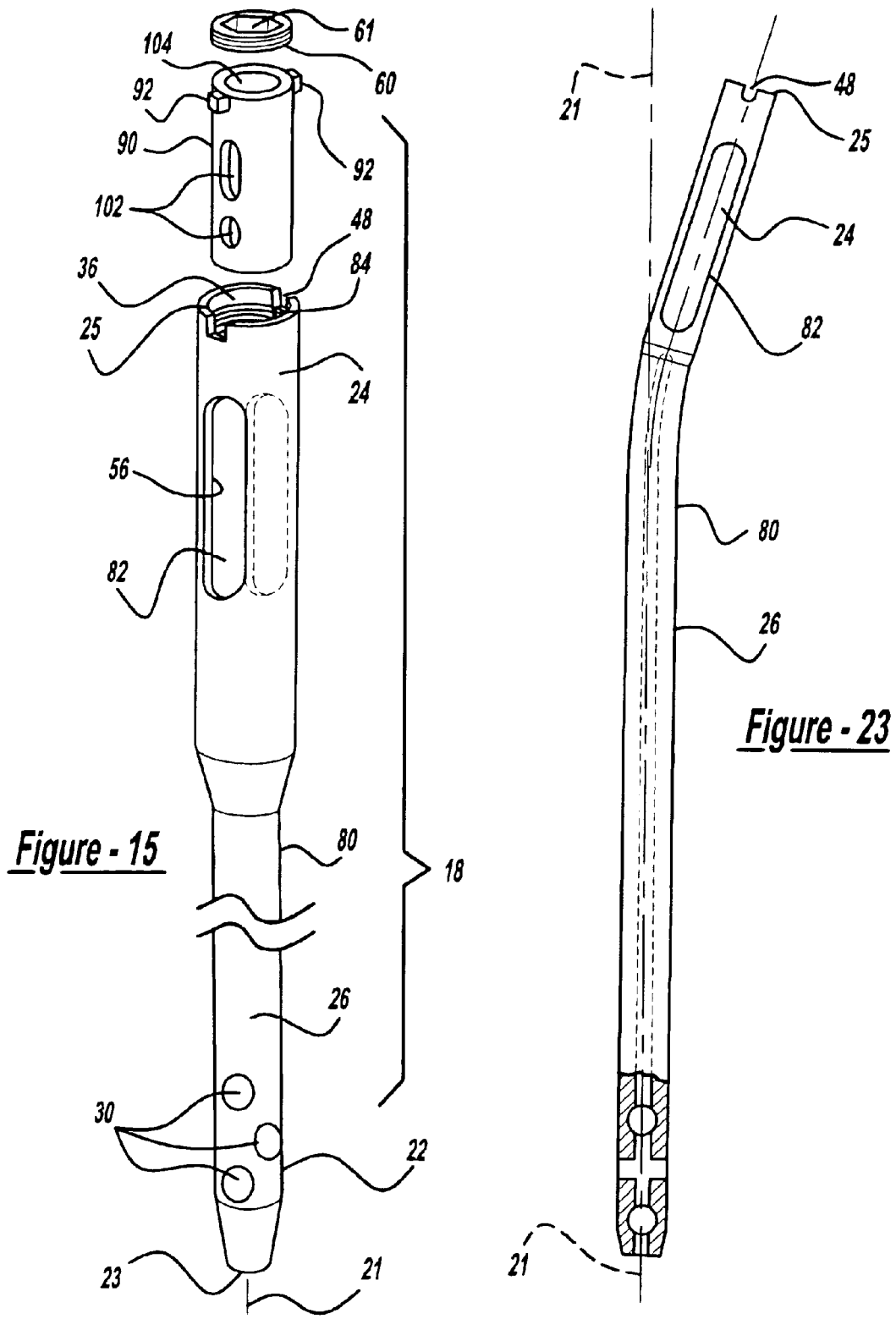
FIG. 15 is an exploded perspective view of a modular nail according to an eighth embodiment of the present invention.
FIG. 23 is a front view of a nail member according to a further embodiment of the present invention.
Figure 16:
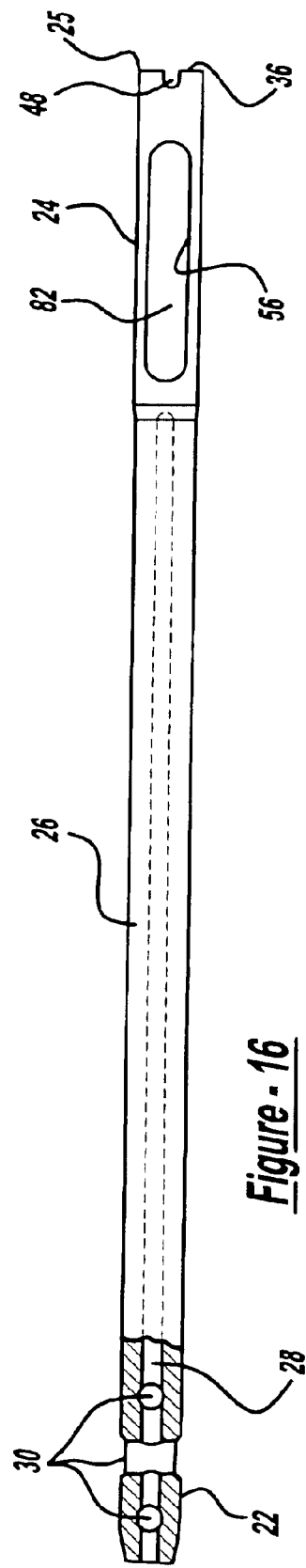
FIG. 16 is a side view of a nail member of the modular nail illustrated in FIG. 15 with a portion shown in section to illustrate a feature thereof.
Figure 17:
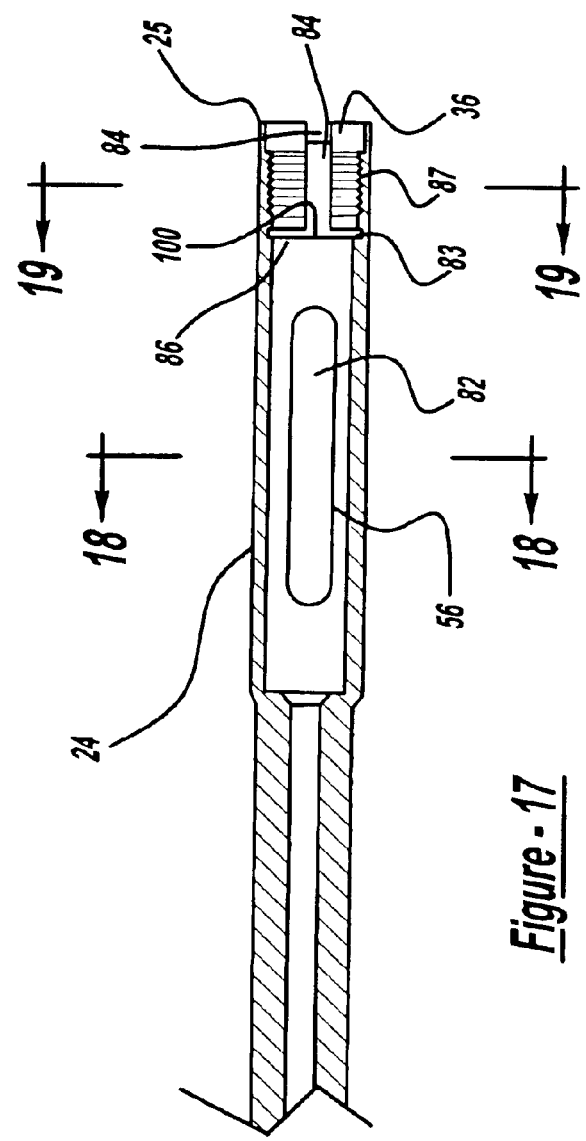
FIG. 17 is a partial sectional view of the nail member of FIG. 16.
Figure 18:
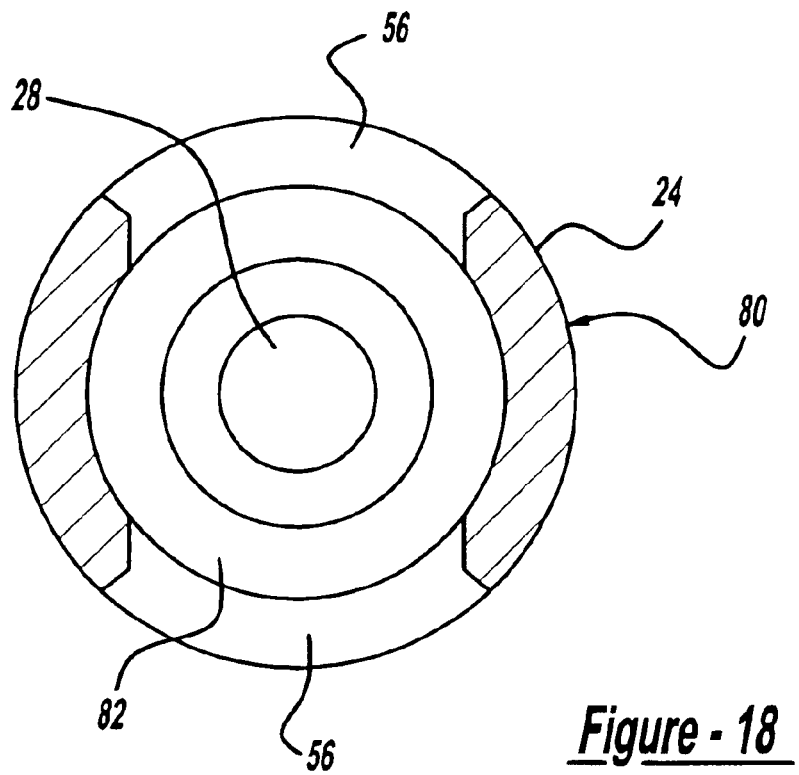
FIG. 18 is a cross-sectional view of the nail member of FIG. 17 taken along line 18—18 of FIG. 17.
Figure 19:
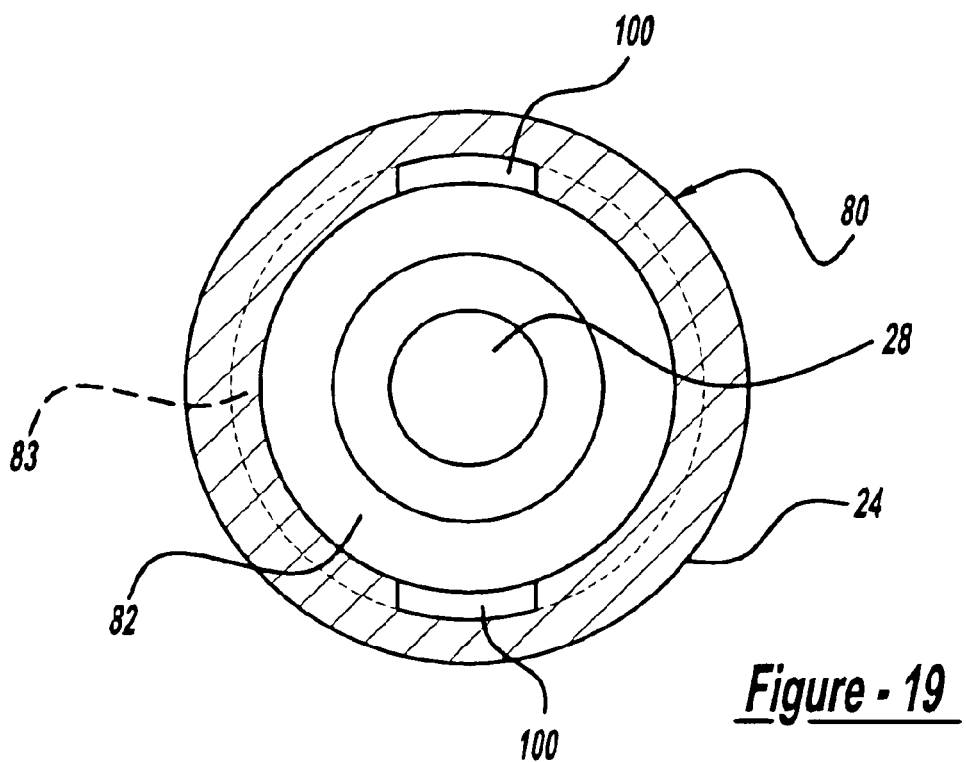
FIG. 19 is a cross-sectional view of the nail member of FIG. 17 taken along line 19—19 of FIG. 17.

A further embodiment of the invention is shown in FIGS. 15–22. FIG. 15 shows a perspective view of a modular intramedullary nail 18 in accordance with an additional embodiment of the present invention. The nail member 80 is similar, in many aspects, to that set forth above. The nail member 80 includes a distal end 22, a proximal end 24, a middle end 26 and a longitudinal passageway 28 therethrough. Further, as with the previous embodiments, holes 30 are formed in the distal end 22 receive fasteners 32 and a pair of notches 48 are formed in the rear edge 25 of the proximal end 24. The nail member 80 of the present embodiment also includes a chamber 82. Again, an opening 36 is located at or near the rear edge 25 of the proximal end 24 and provides access to the chamber 82. The chamber 82 further includes a plurality of threads 87 located on the inner surface 86 of the chamber 82. The chamber 82 is different from that previously disclosed in that it has a pair of grooves or channels 84 extending inwardly along an inner surface 86 of the chamber 82. As shown in FIGS. 17, 19 the grooves or channels 84 extending longitudinally inward in the proximal end 24 of the nail member 80. In the present embodiment, the grooves or channels 84 terminate short of the elongated openings or longitudinal slots 56 located in the proximal end 24 of the nail member 80.

The chamber 82 may also include a radial groove 83 extending circumferentially around the inner surface 86 of the chamber 82. As shown in FIG. 17, the longitudinal grooves 84 terminate at the radial groove 83. The addition of the radial groove 83 makes it easier to form the grooves or channels 84 through a broaching process.

Figure 22:
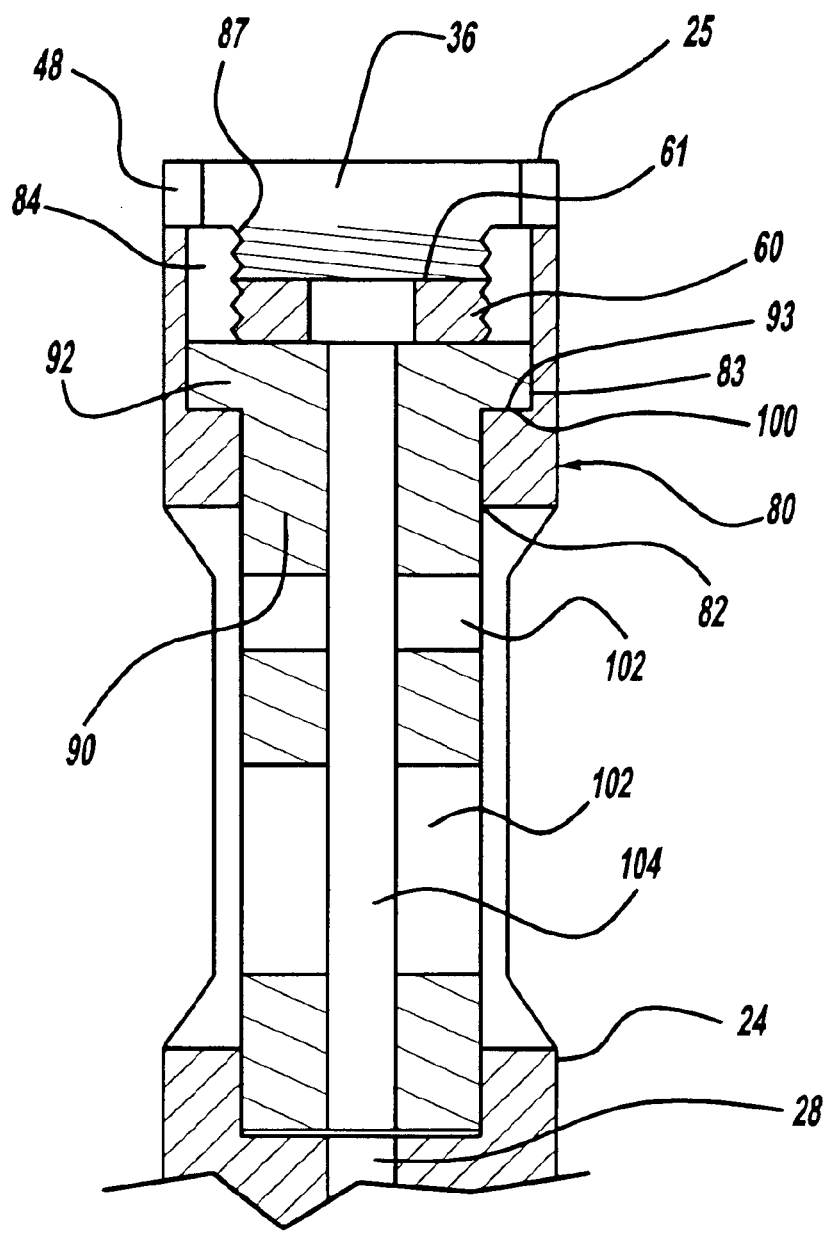
FIG. 22 is a side cross-sectional view of the modular nail and insert assembly of FIG. 15 illustrating the insert secured within the chamber located on the nail member.

As shown in FIGS. 20–22, the insert 90 includes a pair of tabs 92 that jut radially outward and extend beyond the body of the insert 90. While disclosed herein as tabs 92, any outwardly projecting a member that extends outward from the body of the insert 90 and forms a lip 93 thereon is suitable. As will be shown later, the tabs 92 serve as supporting projections that support the insert 90 within the chamber 82. As set forth previously, the insert 90 may have a plurality of openings 102 that receive bone screws or fasteners 32. The tabs 92 cooperate with the grooves 84 to properly orient the insert 90 such that the openings 102 are properly oriented within the chamber 82 to achieve the necessary configuration. As shown with the previous embodiments, the insert 90 further includes a longitudinal passageway 104 extending through the insert from end to end. Once again, insertion and extraction instrumentation, for example a guide wire, extends through the passageway 104 in the insert 90 and through the longitudinal passageway 28 in the nail member 80. The grooves or channels 84 extend inwardly from the open end 36 of the nail member 80. A shelf or ledge 100 is formed adjacent the end of the grooves or channels 84. When a radial groove 83 is used, it forms the shelf or ledge 100. The width of the radial groove 83 is less than the thickness of the tabs 92. Accordingly, the tabs 92 remain aligned within the channels or grooves 84. The shelf or ledge 100 forms a support surface in the proximal end 24 of the nail member 80. As set forth previously, the grooves or channels 84 typically terminate or end before reaching the longitudinal slots 56 formed in the proximal end 24 of the nail member 80. Accordingly, when the insert 90 is placed in the chamber 82, the tabs 92 enter and travel within the grooves 84 until the lips 93 formed underneath the tabs 92 engage the respective shelf or ledge 100. Thus, the tabs 92 perform two functions, they support the insert 90 within the chamber 82 and they operate to properly orient the insert 90 within the chamber 82.

As with the previous embodiment, a locking member 60 may be used to secure the insert 90 within the chamber 82. Once again, the locking member 60 may include an aperture 61 having a hexoganal shape that provides both an opening for the insertion and extraction instrumentation and a socket into which a suitable tool may be inserted to tighten the locking member 60 to secure the insert 90 within the chamber 82. As set forth previously, an end cap may be used to close the open end 36 of the proximal end 24 of nail member 80.

FIG. 23 shows a further alternative embodiment in which the proximal end 24 of the nail member 80 is bowed or bent such that the proximal end 24 is at an angle to the longitudinal axis 21 of the nail member 80.

Figure 24:
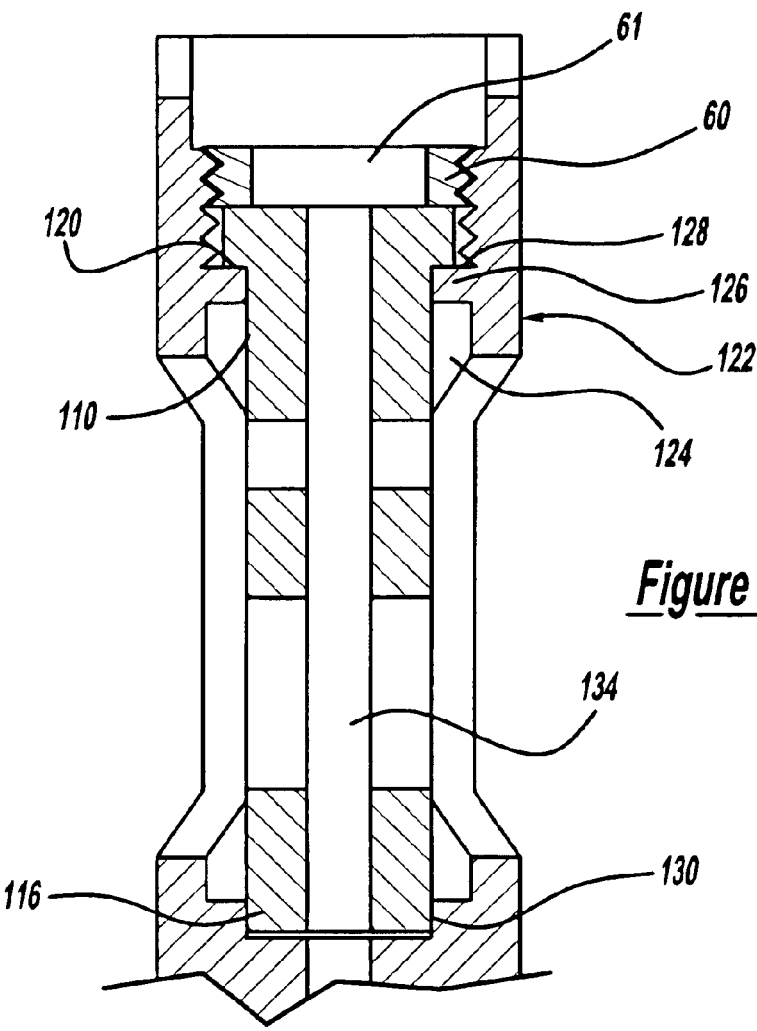
FIG. 24 is a side cross-sectional view of a ninth embodiment of the present invention illustrating an insert secured within a chamber located on the nail member.
Figure 25:
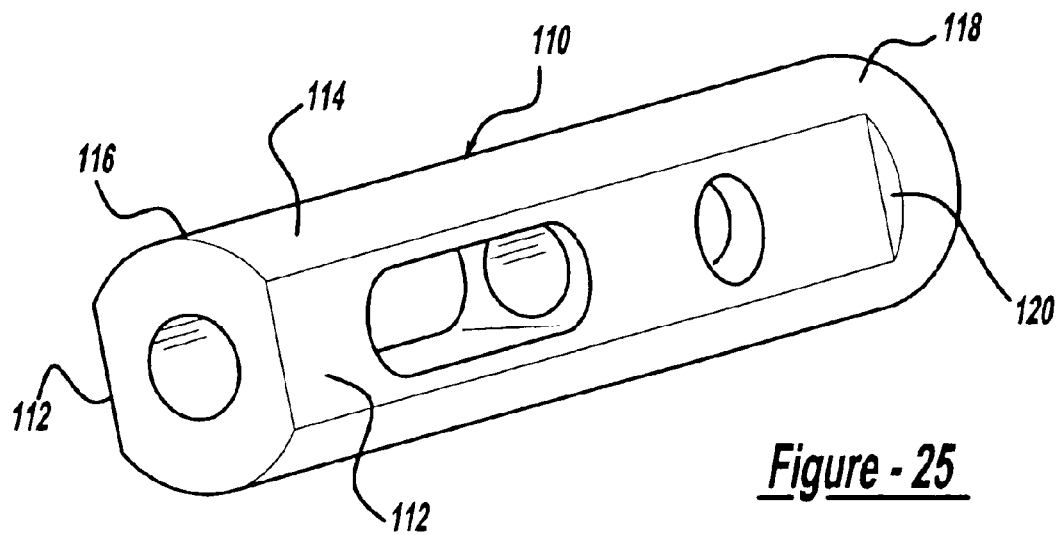
FIG. 25 is a perspective view of an insert for use with the modular nail assembly illustrated in FIG. 24.

FIGS. 24–25 illustrate a further embodiment of the invention. The insert 110 may have a substantially cylindrical shape with opposite flat side surfaces 112 extending along the body 114 of the insert 110. As shown in FIG. 25, the flat side surfaces 112 extend along the body 114 of the insert 110 from the distal end 116 toward the proximal end 118 of the insert 110. The flat side surfaces 112 end and correspondingly form a lip 120 at the proximal end 118 of the insert 110.

Once again the nail member 122 is similar in most aspects to those previously disclosed. In this embodiment, the chamber 124, as shown in FIG. 24, includes an inwardly projecting ledge 126. The ledge 126 forms a seat 128 upon which the lip 120 of the insert 110 rests and is supported. Accordingly, the insert 110 is placed within the chamber 124 such the distal end 116 of the insert 110 is located within a socket 130 formed in the distal end 132 of the chamber 124. The shape of the socket 130 corresponds to the shape of the distal end 116 of the insert 110. Thus, the socket 130 in the present embodiment has a substantially cylindrical shape with two flat sides.

The socket 130 not only laterally supports the distal end 116 of the insert 110 it helps to properly orient the insert 110 in the chamber 124 as well. The insert 110 is longitudinally supported within the chamber 124 by the lip 120 which is seated on the ledge 126. The ledge 126 further engages the flat side surfaces 112 to orient the insert 110. As with the previous embodiments, a locking member 60 engages the nail member 122 to hold the insert 110 in position. The insert 110 also includes a longitudinal passageway 134 extending through the insert 110 from the distal end 116 to the proximal end 118. Again the locking member 60 also includes an aperture 61. Insertion and extraction instrumentation may pass through both the insert 110 and locking member 60 when the insert 110 is held in position within the chamber 124.

The invention has been described in an illustrative manner. It is to be understood that the terminology which has been used is intended to be in the nature of words of description rather than of limitation.

Many modifications and variations of the invention are possible in light of the above teachings. Therefore, within the scope of the appended claims, the invention may be practiced other than as specifically described.

I claim:

1. An intramedullary nail for use with a fastener to repair a bone fracture comprising:
   a nail member, said nail member having a proximal end and a distal end, said proximal end having a chamber located therein, said chamber having an inner surface and at least one groove located in said inner surface;
   an insert, said insert configured for insertion into said chamber, said insert including at least one outwardly extending tab; and
   a locking member, said locking member engaging said nail member to secure said insert within said chamber.

2. An intramedullary nail as set forth in claim 1 including said proximal end having a longitudinal slot extending transversely through said proximal end of said nail member, said slot communicating with said chamber, said groove extending inward on said inner surface of said chamber from a rear edge of said nail member and ending before said slot, a support surface located at the end of said groove such that a said tab enters said groove and engages said support surface when said insert is seated in said chamber.

3. An intramedullary nail as set forth in claim 2 wherein said insert includes at least one opening for receiving a fastener, said opening oriented on said insert such that when said tab engages said groove said opening is aligned with said slot.

4. An intramedullary nail as set forth in claim 1 wherein said insert includes a proximal end and a distal end, said tab positioned on said proximal end.

5. An intramedullary nail as set forth in claim 1 including said insert having a plurality of outwardly extending tabs, said chamber having a plurality of grooves therein, said tabs cooperating with said grooves to support and orient said insert within said chamber.

6. An intramedullary nail member as set forth in claim 1 including said proximal end of said nail member having an opening, said opening communicating with said chamber wherein said insert is placed in said chamber through said opening.

7. An intramedullary nail member as set forth in claim 6 wherein said opening extends transverse a longitudinal axis of said nail member and is located at a rear edge of said nail member such that said insert is inserted within said chamber in the direction of the longitudinal axis of said nail member.

8. An intramedullary nail member as set forth in claim 1 wherein said chamber extends along a longitudinal axis of said nail member from a rear edge of said nail member, said nail member having an opening formed in the proximal end of said nail member, said opening forming a mouth through which said insert is inserted into said chamber, said groove located on an inner surface of said chamber extending inwardly from said opening.

9. An intramedullary nail for use with a fastener to repair a bone fracture comprising:
   a nail member having a distal end and a proximal end, said nail member having a longitudinal passageway extending from said distal end to said proximal end, said nail member further having;
   a chamber located in said proximal end, said proximal end further having an opening providing access to said chamber, said chamber having a proximal end and a distal end, said opening adjacent said proximal end of said chamber, said chamber having an inner surface and a groove located in said inner surface;
   an insert, said insert including an outwardly extending tab, said insert having a proximal end and a distal end, said insert also having an opening extending through said insert at an angle with respect to a longitudinal axis of said insert;
   wherein said tab cooperates with said groove when said insert is placed in said chamber to support said insert within said chamber; and
   a locking member engaging said nail member to secure said insert within said chamber.

10. An intramedullary nail as set forth in claim 9 wherein said chamber includes a plurality of threads in the proximal end thereof; and
   said locking member having an annular shape with a plurality of threads located on an outer surface thereof, said threads cooperating with said threads of said chamber to secure said insert within said chamber.

11. An intramedullary nail as set forth in claim 9 including said nail member having a longitudinal slot in the proximal end of said nail member, said longitudinal slot extending transversely through the proximal end for receiving a fastener that extends through said proximal end of said nail member.

12. An intramedullary nail for use with a fastener to repair a bone fracture comprising:
   a nail member, said nail member having a proximal end and a distal end, said nail member further having a longitudinal passageway extending through said nail member from said proximal end to said distal end and having a chamber located at said proximal end, said chamber having a proximal end and a distal end and including a ledge found in at least a portion of the proximal end of said chamber;
   an insert, said insert adapted to be inserted into said chamber, said insert having a proximal end and a distal end, and having at least one opening extending through said insert at an angle from said longitudinal passageway, said insert further including a lip, said lip engaging said ledge to support said insert in said chamber; and
   a locking member, said locking member, said locking member engaging said nail member to secure said insert within said chamber.

13. An intramedullary nail member as set forth in claim 12 wherein said lip is formed by an outwardly extending tab; and
   said chamber having a longitudinal groove located in an inner surface of said chamber, said groove extending inwardly from said proximal end of said chamber and ending prior to reaching said distal end of said chamber, said ledge formed adjacent the end of said groove such that said tab travels in said groove when said insert is inserted into said chamber.

14. An intramedullary nail member as set forth in claim 12 wherein said insert has a substantially cylindrical shape, said insert further having at least one flat side surfaces extending along said insert from said distal end to a point spaced from the proximal end of said insert, such that the interface formed between the remaining substantially cylindrical shaped portion of said insert and the flat side surface forms said lip.

15. An intramedullary nail member as set forth in claim 14 including said flat side surfacs engaging said ledge when said insert is inserted into said chamber to orient said insert within said chamber.

* * * * *